United States Patent [19]

Carney et al.

[11] 4,216,210

[45] Aug. 5, 1980

[54] FORTIMICINS AM AND AP DERIVATIVES

[75] Inventors: Ronald E. Carney, Gurnee; James B. McAlpine, Libertyville, both of Ill.

[73] Assignee: Abbott Laboratories, North Chicago, Ill.

[21] Appl. No.: 25,253

[22] Filed: Mar. 29, 1979

[51] Int. Cl.$^2$ .................. A61K 31/71; C07H 15/22
[52] U.S. Cl. .................................. 424/180; 424/181; 536/17 R; 536/18
[58] Field of Search ........................ 536/17; 424/180

[56] References Cited

U.S. PATENT DOCUMENTS

| 4,091,032 | 5/1978 | Tadanier et al. | 536/17 |
| 4,124,756 | 11/1978 | Martin et al. | 536/17 |

Primary Examiner—Johnnie R. Brown
Attorney, Agent, or Firm—Robert L. Niblack; Gildo E. Fato; Joyce R. Niblack

[57] ABSTRACT

4,N, 2'-N and 4,2'-Di-N-derivatives of fortimicin AM and fortimicin AP are provided by this invention. The compounds are useful as anti-bacterial agents.

24 Claims, No Drawings

FORTIMICINS AM AND AP DERIVATIVES

BACKGROUND OF THE INVENTION

The aminoglycoside antibiotics are a valuable therapeutic class of antibiotics which include the kanamycins, gentamicins, streptomycins, sagamicins and the more recently discovered fortimicins. While the naturally produced patent antibiotics are generally, in themselves, valuable antibiotics, chemical modifications have been found to improve the activity, either intrinsic activity or activity against resistant strains or against one or more strains the parent antibiotic is not effective against. Thus, chemical modification has provided both alternative therapeutic agents as well as those which are held in reserve because of the resistance problem. And, because of the development of aminoglycoside-resistant strains and inactivation of the parent antibiotics by R-mediated factors which can develop, the search for new therapeutic entities continues.

Further, some of the naturally produced, parent antibiotics, such as fortimicin B and fortimicin E, are primarily useful as intermediates in preparing derivatives which have more potent antibacterial properties than their weakly active parent antibiotics. The present invention provides derivatives of 2 such fortimicins, fortimicins AM and AP.

The fortimicins of this invention are co-produced in the fermentation of *Micromonospora olivoasterospora* ATCC No. 21819,31009 or 31010 according to the method of Nara et al. U.S. Pat. Nos. 3,931,400 and 3,976,768 which disclose the production of fortimicin A and fortimicin B.

Fortimicin AM and fortimicin AP are minor factors which are co-produced with fortimicin A, fortimicin B and a number of other minor assigned patent application Ser. Nos. 025,241; 025,243; 025,247; 025,250; 025,251; and 025,252 filed of even date herewith and with the minor factors disclosed and claimed in commonly assigned, copending United States patent application Ser. Nos. 863,015 and 863,016, both filed Dec. 21, 1977.

The 4-N-derivatives and fortimicin B are disclosed in U.S. Pat. No. 4,091,032. The 2'-N and 4,2'-di-N-derivatives of fortimicin B and fortimicin E are disclosed in commonly assigned, co-pending U.S. Pat. application Ser. Nos. 863,012 and 863,010, both filed Dec. 21, 1977.

SUMMARY OF THE INVENTION

The present invention provides 4-N, 2'-N and 4,2'-di-N fortimicins AM and AP. The compounds of this invention are useful as antibiotics against susceptible gram positive and gram negative bacilli such as *Escherichia coli, Staphylococcus aureus, Pseudomonas aeruginosa, Bacillis subtilis, Proteus vulgaris, Shigella sonnei, Salmonella typhi* and *Klebsiella pneumonia.*

DETAILED DESCRIPTION OF PREFERRED EMBODIMENTS

The compounds of this invention are prepared from fortimicins Am and Ap which are represented by Formula I:

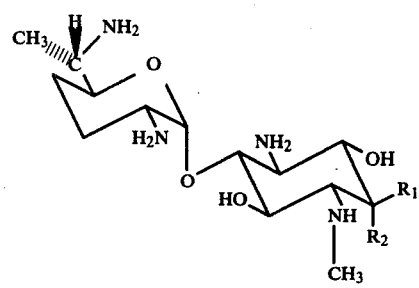

wherein $R_1$ is hydrogen or hydroxy and $R_2$ is hydrogen when $R_1$ is hydroxy and hydroxy when $R_1$ is hydrogen.

When $R_1$ is hydrogen and $R_2$ hydroxy, the compound is fortimicin AM. When $R_1$ is hydroxy and $R_2$ is hydrogen, the compound is fortimicin AP.

Fortimicins AM and AP prepared by the fermentation of *Micromonospora olivoasterospora* as detailed in Examples 1–4.

The compounds of this invention are 4-N-, 2'-N and 4,2'-di-N-fortimicin derivatives and are represented by Formula II:

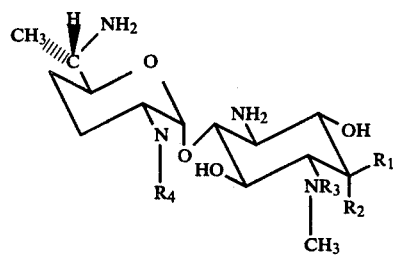

wherein: $R_1$ and $R_2$ are as defined in Formula I, and $R_3$ and $R_4$ are the same or different members of the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, aminohydroxyloweralkyl, N,N-diloweralkylaminoloweralkyl, N-loweralkylaminohydroxyloweralkyl, N,N-diloweralkylaminohydroxyloweralkyl and the pharmaceutically acceptable salts thereof with the limitation that $R_3$ and $R_4$ each cannot be hydrogen.

The term acyl, as used in the above definitions refers to acyl radicals of loweralkylcarboxylic acids represented by the formula

wherein R is loweralkyl, i.e., acetyl, propionyl, butyryl, valeryl, etc.

The terms aminoacyl, hydroxy-substituted aminoacyl, etc., enumerated in the definitions of $R_3$ and $R_4$ for formula II include, but are not limited to as will be obvious to those skilled in the art, naturally occuring amino acids such as glycyl, valyl, alanyl, sarcosyl, leucyl, isoleucyl, prolyl, seryl, and like amino acid residues as well as groups such as 2-hydroxy-4-aminobutyryl and like groups. The amino acid residues included in the above terms, with the exception of glycyl, can be either in the L- or D-configurations or mixtures thereof.

The term "loweralkyl", as used herein, refers to straight or branched chain alkyl radicals containing from 1 to 6 carbon atoms and includes, but is not limited to, methyl, ethyl, n-propyl, iso-propyl, n-butyl, iso-butyl, tert-butyl, n-pentyl, 1-methylbutyl, 2,2-dimethylpropyl, n-hexyl, 2-methylpentyl and the like radicals.

The term "pharmaceutically acceptable salts" refers to the non-toxic acid addition salts of the compounds of Formulae I and II which can be prepared either in situ during the final isolation and purification or by separately reacting the free base with a suitable organic or inorganic acid by methods well known in the art. Representative salts include the mono-, di-, tri-tetra, or other per-salts such as the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and like salts.

The antibiotics of Formula II are effective antibacterial agents against susceptible or sensitive strains of gram-negative and gram-positive bacilli such as *Staphylococcus aureus, Escherichia coli, Pseudomonas aeruginosa, Bacillus subtilis, Proteus vulgaris, Shigella sonnei, Salmonella typhi* and *Klebsiella pneumoniae*. The compounds of Formula II are administered parenterally, i.e., intravenously, intramuscularly, intraperitoneally or subcutaneously for systemic effect in daily dosages of from 20 to 40 mg/kg of body weight daily, preferrably from 25 to 30 mg/kg of body weight daily based on lean body weight as is good medical practice with the aminoglycoside antibiotics and are preferably administered in divided dosages. The compounds can also be administered orally at the above dosages to sterilize the intestinal tract and can further be administered in suppository form.

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain of a specific organism.

Fortimicins AM and AP are prepared by the fermentation of *Micromonospora olivoasterospora* ATCC No. 21819,31009 or 31010 according to the methods described by Nara et al. in U.S. Pat. Nos. 3,931,400 and 3,976,768 for the fermentation of fortimicin A and fortimicin B, and set forth in Examples 1-4 for the fermentation and isolation of The 4-N-acyl fortimicin AM and AP derivatives are prepared following the general procedure used for the preparation of 4-N-acyl derivatives of fortimicins having the fortimicin E stereochemistry for the 4-N-position as disclosed in commonly assigned, co-pending U.S. application Ser. No. 863,010, filed Dec. 21, 1977.

Generally speaking, the 4-N-acyl derivatives can be prepared by reacting 3 moles of salicylaldehyde with fortimicin AM or AP which results in the formation of 1,2',6'-tri-N-salicylaldehyde Schiff base fortimicin AM or AP. The latter can then be aminoacylated by coupling the Schiff base intermediate with a variety of activated carboxylic acid derivatives such as a carboxylic acid anhydride, a carboxylic acid chloride, an active carboxylic acid ester or a carboxylic acid azide.

The active esters may be conveniently prepared by reacting the appropriate carboxylic acid, RCOOH with, for example 1-hydroxybenzotriazole, N-hydroxysuccinimide or N-hydroxy-5-norbornene-2,3-dicarboximide according to the method of M. Fujino et al., *Chem Pharm Bull, Japan* 22: 1857 (1974) wherein R is as defined in formula II for acyl and acyl-containing groups.

For example, the Schiff base fortimicin AM can be aminoacylated with an active ester represented by the formula A-P-Z, i.e., N-benzyloxycarbonylglycyl-N-hydroxysuccinimide active ester (A=ONS, R=COCH$_2$NH—), N-benzyloxycarbonyl-$\beta$-alanyl-N-hydroxy-5-norbornene-2,3-dicarboximide active ester (A=ONB, R=COCH$_2$CH$_2$NH—), N-benzyloxycarbonylsarcosyl-N-hydroxy-5-norbornene-2,3-dicarboximide active ester (A=ONB), R=COCH$_2$N(CH$_3$)—), and N-benzyloxycarbonyl-L-(2-hydroxy-4-amino)butyryl-N-hydroxy-5-norbornene-2,3-dicarboximide active ester (A=ONB, R=COCH(OH)CH$_2$CH$_2$NH—) where the symbol Z refers to the benzyloxycarbonyl group

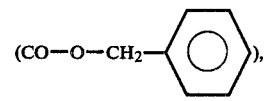

ONB refers to N- hydroxynorbornyldicarboximide and ONS refers to N-benzyloxycarbonyloxy)succinimide.

After the above illustrative couplings, the following intermediates are obtained:4-N-(N-benzyloxycarbonylglycyl)-1,2',6'-tri-N-salicyladehyde Schiff base fortimicin AM; 4-N-(N-benzyloxycarbonyl-$\beta$-alanyl)-1,2',6'-tri-N-salicylaldehyde Schiff base fortimicin AM; 4-N-benzyloxycarbonylsarcosyl)-1,2',6'-tri-N-salicylaldehyde Schiff base fortimicin AM; and 4-N-[N-benzyloxycarbonyl-(L-2-hydroxy-4-aminobutyryl)]-1,2',6'-triN-salicylaldehyde Schiff base fortimicin AM respectively.

It will be readily apparent to those skilled in the art that by substituting the appropriate R$_3$ or R$_4$ group, any of the acyl-containing intermediates for the corresponding final products can be obtained.

The Schiff base intermediates are treated with 0.2 N aqueous hydrochloric acid to cleave the Schiff base protecting groups and the resulting crude trihydrochloride salts are subjected to silica gel chromatography in a solvent system containing ammonium hydroxide which results in the following illustrative, partially deprotected intermediates:4-N-(N-benzyloxycarbonylglycyl)-fortimicin AM; 4-N-(N-benzyloxycarbonyl-$\beta$-alanyl)fortimicin AM; 4-N-(N-benzyloxycarbonylsarcosyl)fortimicin AM; and 4-N-[N-benzyloxycarbonyl-(L-2-hydroxy-4-aminobutryly)]fortimicin AM. The 4-N-protected intermediates are then reacted with N-benzyloxycarbonyl-5-norbornene-2,3-dicarboximide(Z-ONB) to form the corresponding tetra-N-protected intermediates, i.e. tetra-N-benzyloxycarbonyl-4-N-glycylfortimicin AM.

Hydrogenolysis of the tetra-N-protected intermediates over palladium on carbon catalyst(5% Pd/C) in, for example 0.2 N hydrochloric acid in methanol yields the desired final products, i.e. 4-N-glycylfortimicin AM tetrahydrochloride, 4-N-sarcosylfortimicin AM tetrahydrochloride, etc.

4-N-alkylation is readily accomplished by reducing the corresponding acyl, hydroxyacyl or amino-containing acyl product with diborane.

2'-N-acylation is accomplished by rearrangement of the corresponding 4-N-derivative bearing the desired substituent, prepared as described above, by, for example, converting the stable acid addition salts to the free bases with the use of a suitable anion exchange resin and placing the desired 4-N-substituted free base in water which readily rearranges the $C_4$-nitrogen substituent to the nitrogen atom attached to the $C_2'$-carbon. Treatment of the 2'-N-substituted fortimicin with a suitable N-acylating agent such as N-(benzyloxycarbonyloxy)-succinimide, etc., as described above, in a solvent system such as N,N-dimethylformamide-methanol-water, results in 6',1-di-N-protection and the di-N-protected intermediate can then be N-acylated at the 4-position as described above to provide the 4,2'- di-N-acyl derivatives of the fortimicin of this invention, using the term acyl broadly to encompass the "acyl"-containing definitions for $R_3$ and $R_4$ of Formula II.

2'-N-alkylation is achieved, as described above, by reducing the appropriate $C_2'$-N-acyl substituent with a suitable reducing agent such as diborane or a metal hydride such as lithium aluminum hydride. The resulting 2'-N-alkyl derivatives can then be 4-N-acylated as described above to provide 2'-N-alkyl-4-N-acyl derivatives.

The 4,2'-di-N-alkyl derivatives can be prepared by treating the appropriate 4,2di-N-acyl derivatives, suitable N-protected, with a suitable reducing agent as described above and deblocking by hydrogenolysis.

It is to be understood that the terms acy and alkyl have, for the purpose of the above discussion have been used as shorthand references to the terms "loweralkyl" and "acyl" defined on pages 3 and 4 of the specification and to the acyl and alkyl-containing definitions for $R_3$ and $R_4$ is Formula II. This shorthand reference has been used to simplify the above discussion, not to modify the terms as defined.

The following Examples further illustrate the present invention by setting forth the fermentation and isolation of fortimicin AM and AP which is coproduced with fortimicin A, fortimicin B, isofortimicin, fortimicin E and a number of other minor factors.

Fortimicins AM and AP are prepared by the fermentation of *Micromonospora olivoasterospora* ATCC 21819 in a suitable fermentation broth and isolated as described hereinbelow.

EXAMPLE 1

Preparation of Fermentation Broth

6000 Liters of a fermentation broth having the following composition and pH 7 before sterilization is prepared:

| Ingredient | Weight Percent |
|---|---|
| Starch | 4.00 |
| Soybean meal | 2.00 |
| Cornsteep liquor | 0.05 |
| $K_2HPO_4$ | 0.05 |
| $MgSO_4 . 7 H_2O$ | 0.05 |
| KCl | 0.03 |
| $CaCO_3$ | 0.1 |
| Water | to 100.00 |

EXAMPLE 2

Preparation of Inoculum

*Micromonospora olivoasterospora* ATCC 21819 is used as a seed strain and is initially cultured in a first seed medium containing 2% glucose, 0.5% peptone, 0.5% yeast extract and 0.1% calcium carbonate (pH 7.2 before sterilization) by inoculating one loopful of the seed strain into 10 ml of the seed medium in a 50 ml large test tube. Culturing is carried out at 30° C. for 5 days with shaking. Ten ml of the seed culture broth is then inoculated into 30 ml of a second seed medium in a 250 ml Erlenmeyer flask. The composition of the second seed medium is the same as that of the first seed medium. The second seed culturing is carried out at 30° C. for two days with shaking.

Then 30 ml of the second seed culture broth is inoculated into 300 ml of a third seed medium in a two liter Erlenmeyer flask provided with baffles. The composition of the third seed medium is the same as that of the first seed medium and the third seed culturing is carried out at 30° C. for 2 days with shaking. Thereafter, 1.5 liters of the third seed culture broth (corresponding to the contents of five flasks) is inoculated into 15 liters of a fourth seed medium in a 30 liter glass jar fermenter. The composition of the fourth seed medium is the same as that of the first seed medium. Culturing in the jar fermenter is carried out at 30° C. for two days with aeration (15 liters/min) and stirring (350 r.p.m.).

EXAMPLE 3

Production of Fortimicins AM and AP

Fifteen liters of the fourth seed culture broth of Example 2 is inoculated into 150 liters of a main fermentation medium in a 300 liter stainless steel fermenter. The main fermentation medium comprises: 4% starch, 2% soybean meal, 1% corn steep liquor, 0.05% $K_2HPO_4$, 0.05% $MgSO_4.7H_2$), 0.3% KCl and 0.1% $CaCO_3$ and water. (pH 7.0 before sterilization). Culturing in the fermenter is carried out at 30° C. for 4 days with aeration (80 liters/min) and stirring (150 r.p.m.).

EXAMPLE 4

Isolation of Fortimicins AM and AP

To 5000 liters of the fermentation broth, prepared as described above, is added 102 liters of a weakly acidic carboxylic (polymethacrylate) type cation exchange resin in the ammonia form, e.g. Amberlite IRC-50 sold by the Rohm and Haas Company. The mixture is agitated for two hours, during which time the mixture is maintained at pH 6.6 by the addition of sulfuric acid. The ion exchange resin is separated from the broth by centrifugation and then added to a column and backwashed with deionized water until free of extraneous solids. The column is washed with water, then eluted downflow with 1 N ammonium hydroxide. Elutes of pH 9.6 to about 11.3 are collected and concentrated under reduced pressure until excess ammonia is removed. The solution is adjusted to pH 2.0 with hydrochloric acid and treated with 5% (w/v) activated carbon such as Pittsburgh RB carbon sold by Calgon Corporation. The solution is then filtered through a diatomaceous earth mat and the filtrant concentrated under reduced pressure to give a mixture of crude fortimicins and metabolites.

A portion of the crude fortimicin is chromatographed on a column of Dowex CG-50 resin eluted with 0.3 M ammonium hydroxide. Initial and final fractions are discarded. The median fractions are combined, adjusted to pH 2.0 with $H_2SO_4$ and treated with carbon. The mixture is filtered and the pH of the filtrate is adjusted to 6.0 with Dowex WGR resin ($NH_4^+$form) and the resin removed. The solution is concentrated and rechromatographed over a column of Dowex CG-50 resin eluted with 0.125 N ammonium hydroxide. Initial fractions are combined and adjusted to pH 6 with sulfuric acid. Amberlite IR-124 resin (NH$_4$+form) (3 liters) is added and after 30 minutes filtered off and washed well with water. The combined filtrate and washings are treated with 300 g of Pittsburg RB carbon sold by Calgon Corporation. The mixture is filtered. The precipitate is washed with water and the combined filtrate and washings are treated with 4 liters of Dowex WGR resin (NH$_4$+form) and the resin is removed. The filtrate (at pH 6) is concentrated to a residue.

A portion of the residue is chromatographed on a column of Bio Rex 70 resin (NH$_4$+form) (2.5 cm diam×40 cm) and eluted stepwise with 0.3 N, 0.5 N and 1.0 N ammonium hydroxide. The eluate fractions containing the desired components as detected by thin layer chromatography are combined and concentrated to 2.6 g of solid. This is chromatographed on a column of silica gel (2.5 cm diam×58 cm) packed and loaded in chloroform-methanol [1:1 (v/v)] and eluted with the lower phase of a mixture of chloroform-methanol-ammonium hydroxide [1:1:1, (v/v/v)] to give a mixture containing the desired components (660 mg).

A portion (400 mg) of this is chromatographed over a column (1.1 cm diam×60 cm) of silica gel developed with a mixture of methylene chloride-ethanol-ammonium hydroxide [1:2:1, (v/v/v)]. Initial fractions yielded fortimicin AP (111 mg). Proton magnetic resonance spectrum in deuterium oxide with tetramethylsilane as external reference $\delta$1.51 (3H) doublet 7'-CH$_3$; $\delta$2.89 (3H) singlet NCH$_3$ $\delta$5.61 (1H) doublet C$_1$'-H.

Later fractions yielded fortimicin AM (80 mg) proton magnetic spectrum measured similarly to that of fortimicin AP $\delta$1.48 (3H) doublet 7'-CH$_3$; $\delta$2.80 (3H) singlet NCH$_3$ and $\delta$5.58 (1H) doublet C$_1$'-H.

The following examples illustrate the present invention.

EXAMPLE 5

1,2',6'-Tri-N-salicylaldehyde Schiff base fortimicin AM

A solution of 1.3 g of fortimicin and 1.03 g of salicylaldehyde in 30 ml of methanol is refluxed and stirred for 1 hour. The solvent is evaporated under reduced pressure and the residue is dissolved in 30 ml of benzene which is likewise evaporated under reduced pressure. This last process is repeated six times. The residue is dried under high vacuum over KOH pellets to yield the desired product.

EXAMPLE 6

4-N-(N-Benzyloxycarbonylglycyl)-1,2',6',-tri-N salicylaldehyde Schiff base fortimicin A solution of the above prepared 1,2'-di-N-salicylaldehyde Schiff base fortimicin (2.8 g) and N-benzyloxycarbonylglycyl-N-hydroxysuccinimide active ester (2 g) in 25 ml of tetrahydrofuran is stirred at room temperature overnight. The solvent is evaporated under reduced pressure to afford a residue of about 4 g of product.

EXAMPLE 7

4-N-(N-Benzyloxycarbonylglycyl)fortimicin AM

The substance obtained in Example 6(4 g) is dissolved in 500 ml of chloroform and the solution is shaken with 500 ml of 0.2 N aqueous hydrochloric acid. The layers are separated and the chloroform solution is extracted with three 150 ml portions of 0.2 N aqueous hydrochloric acid. The hydrochloric acid extracts are washed in series with three 250 ml portions of chloroform. The chloroform solutions are dried over anhydrous sodium sulfate, filtered, combined and evaporated to leave a residue of nonbasic material which is not characterized.

The aqueous hydrochloric acid extracts are evaporated under reduced pressure at room temperature. The residue is dissolved in 60 ml of methanol and the solvent is likewise evaporated. This last process is repeated six times. The residue is dried over potassium hydroxide pellets under high vacuum to afford crude 4-N-(N-benzyloxycarbonylglycyl)fortimicin AM trihydrochloride salt.

A partial purification of the above residue(2.0 g) by chromatography on 270 g of silica gel using the lower phase of a mixture of chloroform-methanol-concentrated aqueous ammonium hydroxide [1:1:1(v/v/v)] as the eluting solvent system affords a mixture containing the desired product. Further chromatography of this residue(ca 1.4 g) on 180 g of silica gel using the lower phase of a chloroform-methanol-concentrated aqueous ammonium hydroxide-water mixture[2:2:1:1(v/v/v/v)] as the solvent system leads to the separation of several components. Evaporation of the solvent from the early chromatographic fractions leads to the isolation of nonpolar substances which are not further characterized. A next group of fractions yields a small quantity of 4,2'-di-N-(N-benzyloxycarbonylglycyl)fortimicin AM Later fractions of the chromatogram result in the desired product.

EXAMPLE 8

N-Oxybenzyloxycarbonyl-5-norbornene-2,3-dicarboximide

To an ice cooled suspension of 30 g of N-hydroxy-5-norbornene-2,3-dicarboximide in 150 ml of water are added 7.06 g of sodium hydroxide pellets over a period of 10 minutes with stirring. Methanol is added to the ice bath to bring the temperature to −5° C. and the contents of the flask are stirred for 10 minutes. Twenty-three ml of benzyloxycarbonyl chloride are then added to the stirred solution over a period of 15 minutes. The mixture is then stirred at −5° C. for 2 hours and then at room temperature for 24 hours. The reaction mixture is extracted with 400 ml of chloroform and the chloroform extract washed with three 200 ml portions of water. The aqueous washes are then extracted in series with four 200 ml portions of chloroform. The chloroform extracts are dried over anhydrous magnesium sulfate, filtered, combined and evaporated to leave a residue of 39.88 g. The crude material is recrystallized from 95% ethanol. The crystals which form upon cooling are collected on a filter and washed with several small portions of cold ethanol. After drying, 29.11 g of crystalline product is obtained, m.p.126°–127° C. A sample is recrystallized twice more for analysis:m.p. 126°–127° C.; IR(CDCl$_3$) 1800 (shoulder), 1782,1732 cm$^{-1}$: PMR (CDCl$_3$) 7.41(Z-Ar), 6.2(vinyl H), 5.31 (CH$_2$-Z), 3.4(H single proton), 1.7(CH$_2$)ppm.

Anal. Calcd. for C$_{17}$H$_{15}$NO$_5$: C,65.17; H,4.83; N, 4.47. Found: C,65.02; H,4.82; N, 4.26.

EXAMPLE 9

Tetra-N-benzyloxycarbonyl-4-N-glycylfortimicin AM

A solution containing 1.03 g of the above prepared 4-N-(N-benzyloxycarbonyl)glycylfortimicin and 2 g of N-oxybenzyloxycarbonyl-5-norbornene-2,3-dicarbonximide in 56 ml of methanol are stirred at room temperature overnight. Evaporation of the solvent under reduced pressure leaves a residue of about 3 g of crude reactoin mixture. The latter is purified by repeated silica gel column chromatography using benzene-methanol-ethanol [1170:34:136(v/v/v)] and benzene-chloroform-ethyl acetate-n-propanol[13:16:8:3(v/v/v/v)] as the eluting systems.

Combination of the appropriate fractions following the minor unidentified somponenet in the original chromatograms and evaporation of the solvents leave a residue of the desired product. An analytical sample can be obtained by rechromatography of a part of the above product on silica gel using benzene-methanol-ethanol[1170:36:136(v/v/v)] as the eluant.

EXAMPLE 10

4-N-GlycylfortimicinAM tetrahydrochloride salt

A solution of 0.5 g of tetra-N-benzyloxycarbonyl-4-N-lycylortimicinAM in 34 ml of 0.2 N hydrochloric acid in methanol and 16 ml of methanol is hydrogenolyzed over 5% Pd/C for 4 hours. The catalyst is collected on a filter ans washed with methanol. The filtrate is evaporated under reduced pressure, the residue redissolved in methanol and this solvent evaporated. This last procedure is repeated six times to yield the desired product after drying in vacuo over potassium hydroxide pellets.

EXAMPLE 11

4-N-(N-Benzyloxycarbonyl-$\beta$-alanyl)fortimicin AP

A solution of 2.579 g of compound of Example 5 and 2.5 g of the N-benzyloxycarbonyl-$\beta$- alanyl ester of N-hydroxy-5-norbornene-2,3-dicarboximide, prepared by the method of M. Jujino et al., Chem Pharm. Bull. Japan, 22, 1857(1974), in 30 ml of tetrahydrofuran is stirred at room temperature for 25 hours. Evaporation of the solvent under reduced pressure yields about 5 g of crude product.

This material is dissolved in 500 ml of chloroform and the solution is shaken with 500 ml of 0.2 N hydrochloric acid. The layers are separated and the chloroform solution is extracted with three 150 ml portions of 0.2 N hydrochloric acid. The acid extracts are washed in series with three 25 ml portions of chloroform. The chloroform washed are dried over anhydrous magnesium sulfate, filtered, combined and evaporated to yield a non-basic material. The acidic extracts are combined and evaporated under reduced pressure at low temperature. The residue is dissolved in 30 ml of methanol which is also evaporated. This last process is repeated six times to yield a residue of reaction products as the hydrochloride salts after drying in vacuo over potassium hydroxide. The above hydrochloride salts are chromatographed on 170 g of silica gel using the lower layer of a chloroform-methanol-concentrated ammonium hydroxide mixture[1:1:1(v/v/v)] as the eluting solvent. Combination of the fractions containing the desired product and evaporation of the solvents affords a residue which is rechromatographed on 170 g of silica gel using the lower phase of a chloroform-methanol-concentrated ammonium hydroxide-water [2:2:1:1(v/v/v/v)] mixture as the eluting solvent. After combination and evaporation of the solvents from the appropriate fractions, the desired product is obtained

EXAMPLE 12

Tetra-N-benzyloxycarbonyl-4-N-$\beta$-alanylfortimicin AP

A solution of 0.75 g of the above prepared 4-N-(N-benzyloxycarbonyl-$\beta$-alanylfortimicin AP and 1.440 g of N-oxybenzyloxycarbonyl-5-norbornene-2,3-dicarboximide in 40 ml of methanol is stirred at room temperature for 24 hours. Evaporation of the solvent leaves a residue which is chromatographed on 180 ml of silica gel using a methylene chloride-methanol-concentrated ammonium hydroxide mixture [185:15:2(v/v/v)] as the eluent. Combination of the fractions containing the deisred usbstance and evaporation of the solvent leaves a partially purified product. Repeated chromatography of this sample on silica gel using benzene-methanol-ethanol[1170:34:136(v/v/v)], methylene chloride-methanol-concentrated ammonium hydroxide[185:15:2(v/v/v)] yields the desired product.

EXAMPLE 13

4-N-$\beta$-Alanylfortimicin AP tetrahydrochloride

A solution of 0.35 g of the compound of Example 12 in 30 ml of 0.2 N hydrochloric acid in methanol and 20 ml of methanol is hydrogenolyzed over 0.36 g of 5% Pd/C for 4 hours. The catalyst is collected on a filter and washed with several small portions of methanol. The filtrate is evaporated under reduced pressure and the residue is dissolved in 30 ml of methanol which is likewise evaporated under reduced pressure. This last process is repeated six times to afford a residue of about 0.2 g of the desired product after drying in vacuo over potassium hydroxide pellets.

EXAMPLE 14

N-Benzyloxycarbonylsarcosyl active ester of N-hydroxy-5-norbornene-2,3-dicarboximide To a solution of 4.471 g of N-benzyloxycarbonylsarcosine and 3.754 g of N-hydroxy-5-norbornene-2,3-dicarboximide in 15 ml of tetrahydrofuran and 15 ml of dioxane is added N,N-dicyclohexylcarbodiimide in 2 ml of tetrahydrofuran and 2 ml of dioxane according to the method of M. Fujino et al., Chem Pharm. Bull.,Japan, 22, 1857(1974). The mixture is stirred at room temperature overnight. The dicyclohexylurea which precipitates from the reaction mixture is collected on a filter and washed with a total of 20 ml of tetrahydrofuran-dioxane[1:1(v/v)]. Evaporation of the solvent from the filtrate affords 8.523 g of crude product. The substance is recrystallized from isopropanol to yield 4.294 g of the active ester, m.p. 75°–80° C. Concentration of the mother liquors yields an additional 4.125 g of less pure product, m.p. 69°–73° C.

A portion of the first crop is recrystallized for analysis: m.p. 80°–82° C.; IR(CDCl$_3$) 1821,1774,1725,1700(shoulder) cm$^{-1}$; NMR (CDCl$_3$) 7.32(Ar-Z), 6.17(vinyl), 5.13(CH$_2$-Z), 4.3(sar-CH$_2$), 3.35(single H), 3.0(sar-CH$_3$), 1.64(-CH$_2$) ppm.

Anal. Calcd. for C$_{20}$H$_{20}$N$_2$O$_6$: C, 62.49; H,5.24; N, 7.29. Found: C, 62.65; H, 5.28;N, 7.24.

EXAMPLE 15

4-N-(N-Benzyloxycarbonylsarcosyl)fortimicin AM

A solution of 2.4 g of the compound of Example 5 and 2.5 g of the N-benzyloxycarbonylsarcosyl active ester of N-hydroxy-5-norbornene-2,3-dicarboximide of Example 14 in 25 ml of tetrahydrofuran is stirred for 24 hours at room temperature. Evaporation of the solvent under reduced pressure affords a residue of crude product. The residue is taken up in 500 ml of chloroform and the solution is shaken with 500 ml of 0.2 N aqueous hydrochloric acid. The layers are separated and the chloroform solution is extracted with three 150 ml portions of 0.2 N hydrochloric acid. The acid extracts are washed in series with three 250 ml portions of chloroform. The chloroform washes are dried over anhydrous sodium sulfate, filtered, combined and evaporated to leave a non-basic residue.

The acidic extracts are combined and evaporated under reduced pressure at low temperature. The residue is taken up in 30 ml of methanol which is likewise evaporated and the procedure repeated six times. The resulting residue is dried in vacuo over potassium hydroxide pellets.

The above residue is chromatographed on 160 g of silica gel using the lower phase of a chloroform-methanol-concentrated ammonium hydroxide mixture[1:1:1(v/v/v)] as the eluting solvent. The fractions containing the desired product are combined and the solvents evaporated leaving crude product which is rechromatographed on 160 g of silica gel using the lower phase of a chloroform-methanol-concentrated ammonium hydroxide-water mixture[2:2:1:1(v/v/v/v)] as the eluting solvent. After combination of the appropriate fractions and evaporation of the solvents the desired product is obtained.

EXAMPLE 16

Tetra-N-benzyloxycarbonyl-4-N-sarcosylfortimicin AM

A solution of 0.15 g of the product of Example 15 and 0.3 g of N-oxybenzyloxycarbonyl-5-norbornene 2,3-dicarboximide in 10 ml of methanol is stirred at room temperature overnight. Evaporation of the solvent under reduced pressure affords a residue which is chromatographed on 70 g of silica gel using a benzene-methanol-ethanol mixture[1170:34:136(v/v/v)] as the eluent. Combination of the appropriate fractions and evaporation of the solvent yields partially purified tetra N-benzyloxycarbonyl-4-n-sarcosylfortimicin AM. A second chromatogram of this substance on 50 g of silica gel, employing the same solvent system yields the desired product in pure form.

EXAMPLE 17

4-N-Sarcosylfortimicin AM tetrahydrochloride

A solution of 0.15 g of the compound of Example 16 in 12 ml of 0.2 N hydrochloric acid in methanol and 23 ml of methanol is hydrogenolyzed over 0.150 g of a 5% Pd/C catalyst for 4 hours. The catalyst is collected on a filter and washed with methanol. The filtrate is evaporated to dryness under reduced pressure and the residue is dissolved in 20 ml of methanol which is likewise evaporated. The last procedure is repeated six times. The residue is dried in vacuo over potassium hydroxide pellets to afford the desired product.

EXAMPLE 18

4-N-[N-Benzyloxycarbonyl-(L-2-hydroxy-4-aminobutyryl)]-fortimicin AM

The N-hydroxy-5-norbornene-2,3-dicarboximide active ester of L-N-benzyloxycarbonyl-2-hydroxy-4-aminobutyric acid is prepared according to the method of M. Fujino et al. supra. To an ice cold solution of 1.645 g of L-N-benzyloxycarbonyl-2-hydroxy-4-aminobutyric acid and 1.182 g of N-hydroxy-5-norbornene-2,3-dicarboximide in 16 ml of tetrahydrofuran-dioxane [1:1(v/v)], are added, with stirring, 1.374 g of N,N-dicyclohexylcarbodiimide and 5 ml of tetrahydrofurandioxane[1:1(v/v)]. The mixture is stirred at 0° C. for 50 minutes and then at room temperature for 3 hours.

The N,N-dicyclohexylurea produced by the above reaction is collected on a filter and washed with 10 ml of tetrahydrofuran-dioxane[1:1(v/v)]. The filtrate is collected in a flask containing 2.0 g of the compound of Example 5. The reaction mixture is stirred at room temperature for 20 hours. Evaporation of the solvent leaves crude product.

Five and one-half grams of the crude product is dissolved in 500 ml of chloroform and the solution is shaken with 500 ml of 0.2 N hydrochloric acid. The chloroform phase is separated and extracted with three 150 ml portions of 0.2 N hydrochloric acid. The aqueous phase are washed in series with three 250 ml portions of chloroform. The chloroform solutions are dried over anhydrous sodium sulfate, filtered, combined, and evaporated to afford a residue of non-basic substances.

The aqueous extracts are combined and evaporated in vacuo at low temperature. The residue is dissolved in 30 ml of methanol and the solvent evaporated. This last process is repeated six times and the resulting material is dried over potassium hydroxide pellets in vacuo to yield a residue of crude product.

3.5 g of the crude product are chromatographed on 270 g of silica gel using the lower phase of a chloroform-methanol-concentrated ammonium hydroxide[1:1:1(v/v/v)] mixture as the eluent. The fractions containing the desired substance are combined and evaporation of the solvent yields a residue of partially purified product which is rechromatographed on 180 g of silica gel using the lower phase of a chloroform-methanol-concentrated ammonium hydroxide-water [2:2:1:1(v/v/v/v)] mixture as the eluent. Combination and evaporation of the active fractions affords the desired product.

EXAMPLE 19

Tetra-N benzyloxycarbonyl-4-N-(L-2-hydroxy-4-aminobutyryl)-fortimicin AM

A solution of 0.8 g of the above prepared substance and 1.5 g of N-oxybenzyloxycarbonyl-5-norbornene-2,3-dicarboximide in 40 ml of methanol is stirred at room temperature overnight. Evaporation of the solvent from the reaction mixture under reduced pressure affords a residue of about 2 g of crude product which is chromatographed on 180 g of silica gel using a mixture of methylene chloride-methanol-concentrated ammonium hydroxide[185:15:2(v/v/v)] as the eluent. The early fractions of the chromatogram contained the desired substance contaminated with less polar components. From the subsequent fractions, the desired product is isolated after evaporation of the solvent. Repeated silica gel chromatography of the residue of the early fractions above using benzene-methanol-ethanol-acetic acid [1170:35:135:10(v/v/v/v)] and ethyl acetate-ethanol[98:2(v/v)] mixtures affords additional product. After two more chromatograms on silica gel using ethyl acetate-ethanol[98:2(v/v)] as the eluent, the desired product is obtained in pure form.

EXAMPLE 20

4-N-(L-2=Hydroxy-4-aminobutyryl)fortimicin AM tetrahydrochloride

A solution of about 0.2 g of the above prepared compound in 16.3 ml of 0.2 N hydrochloric acid and 8.7 ml of methanol is hydrogenolyzed over a 0.2 g of 5% Pd/C for 4 hours. The catalyst is collected on a filter and washed with methanol. The filtrate is evaporated under reduced pressure and the residue is dissolved in 10 ml of methanol which is likewise evaporated. This last process was repeated six times and the resulting material is dried under high vacuum over potassium hydroxide pellets to afford the desired material.

EXAMPLE 21

Tetra-N-benzyloxycarbonyl-4,2'-N,N'-diglycylfortimicin AM

A solution of the substance contained in the chromatographic fractions preceeding the final product of Example 7 and 0.128 g of N-oxybenzyloxycarbonyl-5-norbornene -2,3-dicarboximide in 3 ml of methanol is stirred at room temperature overnight. Evaporation of the solvent affords a residue which is chromatographed in silica gel using benzene-ethanol-isopropanol[9:1:1(v/v/v)] as the eluting solvent. Combination of the appropriate fraction and evaporation of the solvent leaves a residue which is rechromatographed on silica gel using ethyl acetate-methanol[98:2 v/v)] as the eluting solvent to afford the desired product.

EXAMPLE 22

4,2'-N,N'-Diglycylfortimicin AM tetrahydrochloride

A solution of 0.75 g of the above prepared compound in 6 ml of 0.02 N hydrochloric acid in methanol is hydrogenolyzed over 0.08 g of 5% Pd/C for four hours. The catalyst is collected on a filter and washed with several portions of methanol. The filtrate is evaporated under reduced pressure and the residue redissolved in 15 ml of methanol which is likewise evaporated. This last procedure is repeated six times and the desired product dried in vacuo pver potassium hydroxide pellets.

EXAMPLE 23

4N-(β-Aminoethyl)fortimicin AM

A stirring solution of 4-N-glycylfortimicin (2.0 g) in tetrahydrofuran (80 ml) is treated with 1.22 g of lithium aluminum hydride. The stirring reaction mixture is refluxed for 20 hours and then the excess lithium aluminum hydride is consumed by the careful addition of water. The insoluble material is sedimented by centrifugation. The pellet is suspended in 50 ml of water and centrifuged. The combined supernatants are taken to dryness under reduced pressure to yield crude product which is chromatographed on a column (2.0×40 cm) of cation exchange resin, carboxylic type, e.g., Bio-Rad Laboratories, Bio-Rex 70,100-200 mesh, ammonia form, and eluted with a gradient of water to 1 N ammonium hydroxide. Fractions containing the desired product are concentrated to a small volume and lyophilized to give the desired product.

The in vitro antibiotic activity is determined by a two-fold agar dilution method using 10 ml per petri plate of Mueller-Hinton agar. The agar is inoculated with one loopful (0.001 ml loop) of a 1:10 dilution of a 24 hour broth culture of the indicated test organism and incubated at 37° C. for 24 hours.

The compounds of this invention are active as systemic antibiotics when injected by parenteral routes of administration, i.e., by the intramuscular, intravenous, intraperitoneal or subcutaneous routes of administration. The compounds can also be administered orally in those instances where it is desirable to sterilize the intestinal tract and can also be applied topically or in suppository form.

Preparations according to this invention for parenteral administration include sterile aqueous or non-aqueous solutions, suspensions, or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized, by, for example, filtration through a bacteria-retaining filter, by incorporating sterilizing agents into the compositions and the like. They can also be manufactured in the form of sterile solid compositions which can be dissolved in sterile water, or some other sterile injectable medium immediately before use.

Solid dosage forms for oral administration including capsules tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents compositions can also include adjuvants, such as wetting agents, emulsifying and suspending agents, and sweetening, flavoring and perfuming agents.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 20 to 40 mg/kg of body weight daily, based on lean body weight are administered to a mammalian patient suffering from an infection caused by susceptible organism.

The invention claimed is:

1. A fortimicin selected from the group consisting of 4-N, 2'-N and 4,2'-di-N-derivatives of fortimicin AM and fortimicin AP represented by the formula:

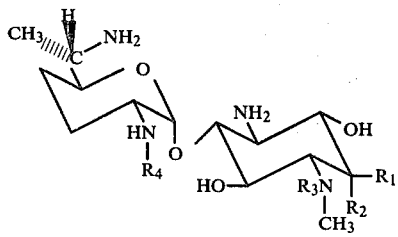

wherein: $R_1$ is hydrogen or hydroxy; $R_2$ is hydroxy when $R_1$ is hydrogen and is hydrogen when $R_1$ is hydroxy; and $R_3$ and $R_4$ are the same or different members of the group consisting of acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl, N,N-diloweralkylaminohydroxyloweralkyl, with the limitation that $R_3$ cannot be hydrogen when $R_4$ is hydrogen; and the pharmaceutically acceptable salts thereof.

2. A compound of claim 1 wherein $R_1$ is hydrogen and $R_2$ is hydroxy.

3. A compound of claim 2 wherein $R_4$ is hydrogen.

4. A compound of claim 3: 4-N-glycylfortimicin AM or a pharmaceutically acceptable salt thereof.

5. A compound of claim 3: 4-N-sarcosylfortimicin AM or a pharmaceutically acceptable salt thereof.

6. A compound of claim 3: 4-N-beta-alanylfortimicin AM or a pharmaceutically acceptable salt thereof.

7. A compound of claim 3: 4-N-(L-2-hydroxy-4-aminobutyryl)fortimicin AM or a pharmaceutically acceptable salt thereof.

8. A compound of claim 3: 4-N-beta-aminoethylfortimicin AM or a pharmaceutically acceptable salt thereof.

9. A compound of claim 2 wherein $R_3$ is hydrogen.

10. A compound of claim 9: 2'-N-glycylfortimicin AM or a pharmaceutically acceptable salt thereof.

11. A compound of claim 2 wherein neither $R_3$ or $R_4$ are hydrogen.

12. A compound of claim 11: 4,2'-di-N-glycylfortimicin AM or a pharmaceutically acceptable salt thereof.

13. A compound of claim 1 wherein $R_1$ is hydroxy and $R_2$ is hydrogen.

14. A compound of claim 13 wherein $R_4$ is hydrogen.

15. A compound of claim 14: 4-N-glycylfortimicin AP or a pharmaceutically acceptable salt thereof.

16. A compound of claim 14: 4-N-sarcosylfortimicin AP or a pharmaceutically acceptable salt thereof.

17. A compound of claim 14: 4-N-beta-alanylfortimicin AP or a pharmaceutically acceptable salt thereof.

18. A compound of claim 14: 4-N-(L-2-hydroxy-4-aminobutyryl)fortimicin AP or a pharmaceutically acceptable salt thereof.

19. A compound of claim 14: 4-N-beta-aminoethylfortimicin AP or a pharmaceutically acceptable salt thereof.

20. A compound of claim 13 wherein $R_3$ is hydrogen.

21. A compound of claim 20: 2'-N-glycylfortimicin AP or a pharmaceutically acceptable salt thereof.

22. A compound of claim 13 wherein neither $R_3$ nor $R_4$ are hydrogen.

23. A compound of claim 22: 4.2'-di-N-glycylfortimicin AP or a pharmaceutically acceptable salt thereof.

24. A pharmaceutical composition comprising an antibacterially effective amount of a compound of claim 1 and a pharmaceutically acceptable carrier or diluent.

* * * * *